April 22, 1941. A. E. GUDE Plant Pat. 462
HYBRID TEA ROSE
Filed Dec. 10, 1940
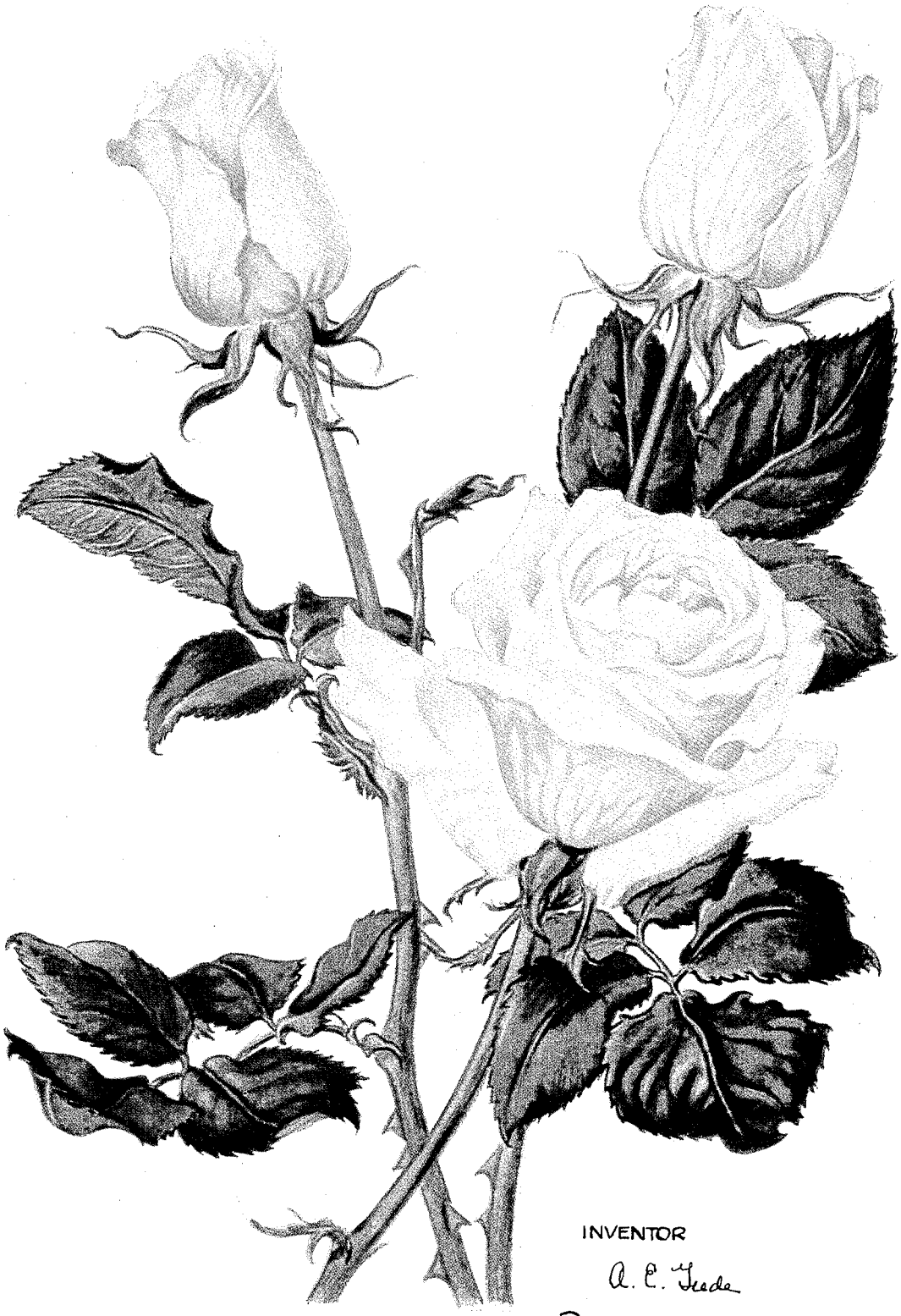
INVENTOR
A. E. Gude
Pattison, Wright & Pattison
ATTORNEYS Patented Apr. 22, 1941

Plant Pat. 462

UNITED STATES PATENT OFFICE

462

HYBRID TEA ROSE

Adolph E. Gude, Rockville, Md., assignor to A. Gude Sons Company, Inc., Washington, D. C., a corporation of the District of Columbia Application December 10, 1940, Serial No. 369,501

1 Claim. (Cl. 47—61)

My new invention relates to a rose colored hybrid tea rose and is an improvement over the Red Radiance of which it is a sport.

This rose was discovered by me as a branch of a plant of Red Radiance and it differs from its parent in several important points. The buds and blooms are of a clear deep rose pink and are larger than those of its parent. The buds of the rose are vase-shaped rather than globular as are those of the parent.

I have asexually reproduced this new variety over a period of time sufficiently long to be able to definitely declare that its distinguishing characteristics are firmly fixed.

The accompanying illustrations show three specimens of this new variety in various stages of development of opening together with portions of the stems and leaves in approximately their exact true colors.

A detailed description of my new variety of rose follows and color plate references therein indicate Ridgway's Color Standards and nomenclature.

*The plant*

Growth: very vigorous upright bush, attaining a height of four feet or more. Prolific bloomer.

Stem: Long, straight, stout.

*Thorns.*—Large sharp, downward-pointing red.

Foliage: Abundant and very sturdy.

*Leaves.*—Compound, usually composed of five leaflets.

*Leaflets.*—*Shape*—ovate with acuminate apex and rounded base; edges sharply serrated. *Size*—terminal leaflets average about 2¾" by 1½" to 1¾" wide. *Color*—upper surface, Spinach Green (Plate V), under surface, Pois Green (Plate XLI); edges sometimes tinged with red.

*Rachis.*—Heavy, grooved and red tinged above; smooth beneath.

*Stipules.*—Long and clinging, slender pointed tips sometimes curved.

*Peduncle.*—Long, very sturdy; often covered with tiny prickles, though sometimes entirely smooth. *Color*—Cress Green (Plate XXXI), frequently bronzed on one side.

*Sepals.*—Long pointed, sometimes inclined to be foliaceous.

*The flower*

Bud:

*Form.*—Long and vase-shaped.

*Color.*—Rose Color (Plate XII).

*Opening.*—Slowly and evenly.

Blooms:

*Size.*—Large, averaging 5½ to 6 inches across.

*Form.*—High centered, full.

*Petalage.*—Double, having about 30 petals.

*Petals.*—*Size*—outer petals about 2½" long by 2¼" wide; of excellent substance. *Shape*—obovate, distinctly ruffled edges, with single notch at top of most petals. *Color*—Rose Color (Plate XII) on upper surfaces, Rose Pink (Plate XII) to Deep Rose Pink (Plate XII) on under surfaces.

*Longevity.*—Lasts well on the bush and exceedingly well as cut flower.

*Behavior.*—Retains form and petals cling tenaciously.

*Fragrance.*—Distinct and very pleasant, similar to that of the parent, but intensified.

*Reproductive organs*

Stamens: Many, irregularly bunched around pistils.

*Filaments.*—Of varying lengths, approximately Ochraceous Buff in color (Plate XV).

*Anthers.*—Medium size. *Color*—approximately Yellow Ocher (Plate XV).

Pistils: Numerous, closely bunched.

*Styles.*—Uneven, shorter than stamens, Light Greenish Yellow (Plate V).

*Stigmas.*—Approximately Primuline Yellow (Plate XXI).

Hips: Large, tapering gradually to stem.

Having thus described my invention I claim:

A new and distinct variety of hybrid tea rose, characterized primarily by its large blossoms of a clear deep rose color, its vase-shaped bud, and its free and vigorous growth.

ADOLPH E. GUDE.